United States Patent [19]
Ikeda et al.

[11] Patent Number: 5,958,977
[45] Date of Patent: *Sep. 28, 1999

[54] PHOSPHORIC ACID-AMINO ACID COMPLEX SALT AND ADDITIVE COMPOSITION CONTAINING THE SALT AND USED IN FEED FOR RUMINANT MAMMALS

[75] Inventors: Toru Ikeda; Toshihide Yukawa, both of Kawasaki, Japan

[73] Assignee: Ajinomoto Co., Inc., Tokyo, Japan

[ * ] Notice: This patent is subject to a terminal disclaimer.

[21] Appl. No.: 08/687,428

[22] PCT Filed: Dec. 8, 1995

[86] PCT No.: PCT/JP95/02530

§ 371 Date: Aug. 9, 1996

§ 102(e) Date: Aug. 9, 1996

[87] PCT Pub. No.: WO96/17822

PCT Pub. Date: Jun. 13, 1996

[30] Foreign Application Priority Data

Dec. 9, 1994 [JP] Japan .................................. 6-306385

[51] Int. Cl.$^6$ .......................... C07C 229/26; A23K 1/18; A23K 1/16; A23K 1/175
[52] U.S. Cl. .............................. 514/564; 514/76; 514/77; 514/558; 514/905; 424/438; 424/442; 426/74; 426/656; 426/807; 562/8; 562/562
[58] Field of Search ............................ 424/438, 601–606, 424/442; 514/75, 561, 564, 558, 905, 76, 77; 426/531, 648, 807, 74, 656; 562/8, 562

[56] References Cited

U.S. PATENT DOCUMENTS

| | | |
|---|---|---|
| 4,351,735 | 9/1982 | Buddemeyer et al. ..................... 252/1 |
| 4,446,055 | 5/1984 | Shah et al. ................................ 516/24 |
| 5,631,031 | 5/1997 | Meade ......................................... 426/2 |
| 5,635,198 | 6/1997 | Nishimura et al. ..................... 424/438 |
| 5,744,178 | 4/1998 | Ikeda et al. ................................ 426/2 |
| 5,763,657 | 6/1998 | Hijiya et al. ............................ 562/561 |
| 5,795,585 | 8/1998 | Ikeda et al. ............................. 424/438 |
| 5,871,773 | 2/1999 | Rode et al. .............................. 424/438 |

FOREIGN PATENT DOCUMENTS

| | | |
|---|---|---|
| 63-98357 | 4/1988 | Japan . |
| 5-84042 | 4/1993 | Japan . |

OTHER PUBLICATIONS

U.S. application No. 08/919,500, filed Aug. 28, 1997, Pending.

U.S. application No. 08/948,087, filed Oct. 9, 1997, Pending.

U.S. application No. 08/640,854, filed May 13, 1996, Pending.

Primary Examiner—John Pak
Attorney, Agent, or Firm—Oblon, Spivak McClelland, Maier & Neustadt, P.C.

[57] ABSTRACT

A novel phosphoric acid-amino acid complex salt is provided which manifests insolubility in a neutral or alkaline aqueous solution and solubility in an acidic aqueous solution and has a basic amino acid, an alkaline earth metal, and phosphoric acid as main components thereof. An additive composition containing the complex salt and used in a feed for ruminant mammals excels in protection in the first compartment of the stomach of a ruminant mammal and solubility in the fourth compartment of the stomach. This additive composition improves the nutrition of the feed with respect to such a basic amino acid as lysine, a substance frequently missing in the feed for ruminant mammals.

10 Claims, 2 Drawing Sheets

PHOSPHORIC ACID-AMINO ACID COMPLEX SALT AND ADDITIVE COMPOSITION CONTAINING THE SALT AND USED IN FEED FOR RUMINANT MAMMALS

This application is a 371 of PCT/JP95/02530, filed on Dec. 8, 1995.

TECHNICAL FIELD

This invention relates to an additive composition to be used in a feed for ruminant mammals. More particularly, it relates to an additive composition for use in a powdery or homogeneously granular feed for ruminant mammals which is stable in the first compartment of the stomach, i.e., rumen of a ruminant mammal and is capable of releasing a basic amino acid in the fourth compartment of the stomach, i.e., abomasum, and the subsequent digestive organs of the ruminant mammal.

BACKGROUND ART

In such ruminant mammals as cows and sheep, when such biologically active substances as amino acids and vitamins are directly administered orally, they are mostly hydrolyzed by microorganisms inhabiting rumen and are prevented from being utilized effectively. Such a rumen bypass preparation for ruminant mammals as is capable of protecting such a biologically active substance from the hydrolysis by the microorganisms in the rumen and enabling it to be digested and absorbed in the abomasum and the subsequent digestive organs, therefore, is important in the field of feeds, nutritive agents, and animal medicines for ruminant mammals.

For the manufacture of ruminant feed additives containing biologically active substances, methods which comprise dispersing a biologically active substance in a matrix formed of such a protective substance as a hydrophobic substance like oil or fat or a basic macromolecular substance and granulating the resultant composite or methods which comprise coating seeds containing a biologically active substance with such an acid sensitive substance as a hydrophobic substance like oil or fat or a basic macromolecular substance have been proposed to date.

As one of the methods resorting to the dispersion of a biologically active substance in a protective substance, JP-A-60-168,351, for example, proposes a method which comprises causing a biologically active substance to incorporate therein not less than 20% by weight of calcium carbonate and not less than 10% by weight of an aliphatic monocarboxylic acid having 14 or more carbon atoms, a cured oil or fat, etc. as well and granulating the resultant mixture. JP-B-59-10,780 proposes another method which comprises dispersing 30 to 50% by weight of a biologically active substance in a protective substance composed of 10 to 35% by weight of a salt of an aliphatic monocarboxylic acid having 14 to 22 carbon atoms or ricinoleic acid and the balance of an aliphatic monocarboxylic acid having 14 to 22 carbon atoms, ricinoleic acid, a cured oil or fat, etc.

As one of the methods resorting to coating a biological substance with a hydrophobic protective substance, JP-A-63-317,053, for example, proposes a method which comprises coating a biologically active substance with a protective agent composed of an aliphatic monocarboxylic acid having 12 to 24 carbon atoms, a cured oil or fat, lecithin, and a glycerin aliphatic ester.

As methods resorting to coating a biologically active substance with an acid sensitive protective substance, JP-A-54-46,823, for example, proposes a method which fulfills the coating with a coating composition containing a film-forming basic macromolecular substance and JP-A-04-217,625 proposes a method which resides in spray coating zein in the form of a water emulsion or a water dispersion.

The methods involving the dispersion of a biologically active substance in a protective substance, however, require the content of the biologically active substance to be appreciably lowered with due respect to the capacity for protection because the biologically active substance is present in the proximity of the surface of particles. In view of the fact that the biologibally active substance, when soluble in water, has a retention time in the range of ten-odd hours to several days in the rumen, the methods incur difficulty in affording necessary protection.

A method which resides in coating seeds containing a biologically active substance with an acid sensitive macromolecular substance or a hydrophobic protective substance has been also proposed. From the point of view of the manufacture of a compound feed which has been thriving in recent years, however, the product of this method does not deserve to be called a general-purpose feed additive composition because it often suffers the granules and/or the coating thereof to sustain breakage under the mechanical impact exerted thereon during the courses of mixture of the seeds with other feed composition and granulation of the resultant mixtion and, as a result, compels itself to sacrifice the stability of retention in the rumen of a ruminant.

In order for the feed additive to be capable of tolerating such mixture with other feed composition or such granulation as mentioned above, it properly ought to be in the form of a powder or homogeneous granules endowed with the quality of precluding release of a biologically active substance in the rumen and, at the same time, permitting separation by solution of the biologically active substance in the abomasum and the subsequent digestive organs. When a basic amino acid is used for the purpose of improving the nutrition of a feed, however, any substance containing the basic amino acid, assuming the form of a powder or homogeneous granules, and manifesting neutrality, insolubility, and solubility in acids has not yet been found except phospho-tungstates.

P-A-63-98,357 discloses an additive composition which is coated with the salt of a basic amino acid and an acidic phosphate and used in a feed for ruminant mammals. The salt of the basic amino acid which is an alkaline earth metal salt of an acidic phosphoric acid in the invention of the patent publication just mentioned is a substance analogous to the phosphoric acid-amino acid complex salt of the present invention. In the salt of the basic amino acid with the alkaline earth metal salt of the acidic phosphoric acid of the invention just mentioned, the molar ratio of phosphoric acid, alkaline earth metal, and basic amino acid is 1:0.5:1 through 2. Thus, this salt is different from the complex salt of phosphoric acid, alkaline earth metal salt, and basic amino acid contemplated by the present invention. The salt of the basic amino acid with the alkaline earth metal salt of acidic phosphoric acid according to the invention just mentioned undergoes decomposition in water with the elapse of time and gives rise to the secondary phosphate of the alkaline earth metal and the primary phosphate of the basic amino acid or the secondary phosphate of the basic amino acid. Since the phosphate of the basic amino acid manifests extremely high solubility in water, it is substantially neutral and soluble in water from the point of view of the solubility of the basic amino acid.

Phosphoric acid forms diverse salts with alkaline earth metals. Some of these salts manifest insolubility in neutral to alkaline water and solubility in acidic water. Calcium secondary phosphate, magnesium tertiary phosphate, and the like, for example, are known to deposit scaly matter and cause mechanical troubles in devices included in the facilities of the fermentation industry which use phosphoric acid copiously. Magnesium ammonium phosphate manifests a similar nature. A complex salt which consists of 1 mol of phosphoric acid, 1 mol of an alkaline earth metal, and 1 mol of a basic amino acid in consequence of the substitution of an ammonium ion as a basic ion for an equivalent basic amino acid and a tertiary phosphoric acid and/or a secondary phosphate which is composed of 1 to 1.45 mols of an alkaline earth metal and 1 to 0.05 mol of a basic amino acid per mol of phosphoric acid have never been known to exist. A phosphoric acid-amino acid complex salt which is an alkaline earth metal salt of condensed phosphoric acid and metaphosphoric acid and which contains a basic amino acid and an alkaline earth metal at a ratio of 0.02 to 0.3 vs. 0.7 to 0.98 by equivalent ratio has never been known to exist.

The task which this invention aims to fulfill resides in creating a composition which incorporates a basic amino acid therein with consideration for safety and economy, which does not dissolve in the first compartment of the stomach of a ruminant mammal, which dissolves out the basic amino acid in the fourth compartment of the stomach and the subsequent digestive organs and causes the separated basic amino acid to be digested and absorbed efficiently, and which is in the form of a powder or homogeneous granules.

DISCLOSURE OF THE INVENTION

The present inventors, after continuing a strenuous effort with a view to accomplishing the task mentioned above, have found that a complex salt composed of a basic amino acid, an alkaline earth metal, and phosphoric acid assumes the form of a powder insoluble in neutral to alkaline water and soluble in acidic water and combines insolubility in the rumen of a ruminant and veritably outstanding solubility in abomasum and the subsequent digestive organs. The present invention has been perfected as a result.

To be specific, the essence of this invention consists in a phosphoric acid-amino acid complex salt composed of a basic amino acid, an alkaline earth metal, and an orthophosphoric acid as represented by the following general formula (1):

$$R_a M_b H_c PO_4 \cdot nH_2O \tag{1}$$

(wherein R stands for a basic amino acid hydrogen cation, M for an alkaline earth metal, a for a numerical value in the range of 0.05 to 1, b for a numerical value in the range of 1 to 1.47, c for a numerical value in the range of 0 to 0.3, providing a, b, and c collectively satisfy the expression, $a+2\times b+c=3$, and n for a numerical value in the range of 0 to 10), composed of a basic amino acid, an alkaline earth metal, and condensed phosphoric acid as represented by the following general formula (2):

$$R_a M_b H_c PO_4(PO_3)_m \cdot nH_2O \tag{2}$$

(wherein R stands for a basic amino acid hydrogen cation, M for an alkaline earth metal, a for a numerical value in the range of $0.02\times(m+3)$ to $0.3\times(m+3)$, b for a numerical value in the range of $0.35\times(m+3)$ to $0.49\times(m+3)$, c for a numerical value in the range of 0 to $0.2\times(m+3)$, providing a, b, and c collectively satisfy the expression, $a+2\times b+c=m+3$, m for an integer in the range of 1 to 20, and n for an integer in the range of 0 to 10), or composed of a basic amino acid, an alkaline earth metal, and metaphosphoric acid as represented by the following general formula (3):

$$R_a M_b H_c (PO_3)_m \cdot nH_2O \tag{3}$$

(wherein R stands for a basic amino acid hydrogen cation, M for an alkaline earth metal, a for a numerical value in the range of $0.02\times m$ to $0.3\times m$, b for a numerical value in the range of $0.35\times m$ to $0.49\times m$, c for a numerical value in the range of 0 to $0.2\times m$, providing a, b, and c collectively satisfy the expression, $a+2\times b+c=m$, m for an integer in the range of 3 to 50, and n for an integer in the range of 0 to 20), i.e. a phosphoric acid-amino acid complex salt insoluble in a neutral or alkaline aqueous solution and soluble in an acidic aqueous solution, an additive composition for use in a feed for ruminant mammals, characterized by containing the phosphoric acid-amino acid complex salt and having an ability to form homogenous granules, and a method for the production of the additive composition. Now, this invention will be described in detail below.

DETAILED DESCRIPTION OF THE INVENTION

Figure 1:
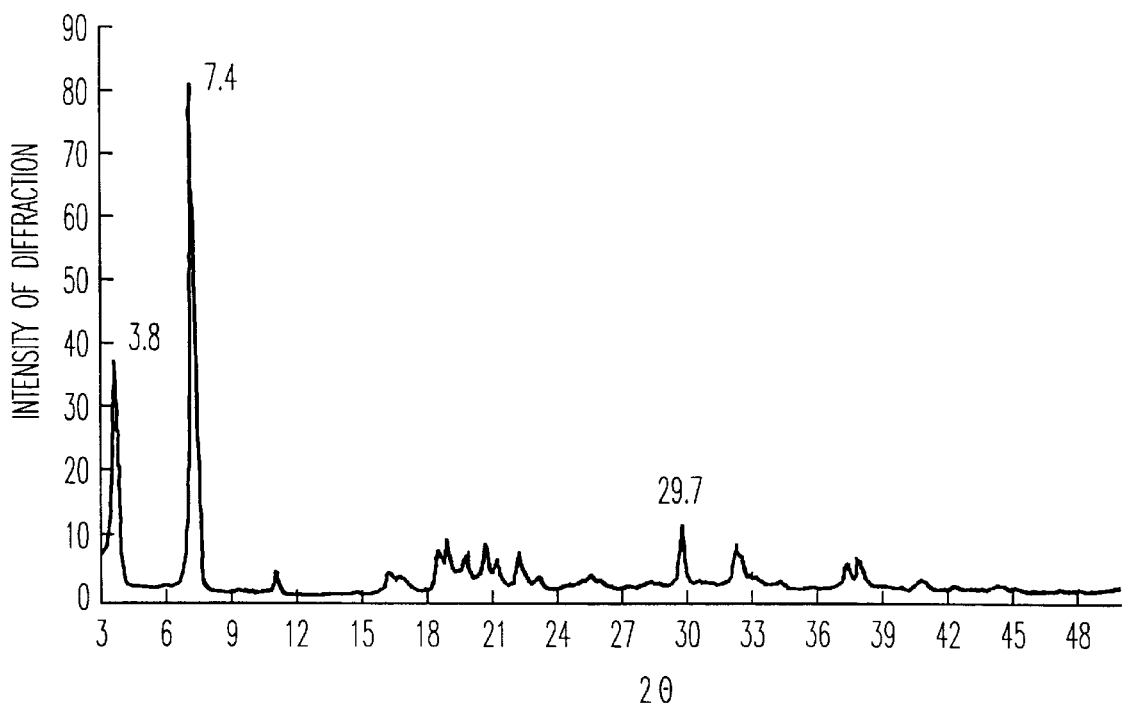
FIG. 1 is a powder X-ray diffraction chart of the novel phosphoric acid-amino acid complex compound of this invention obtained in Example 1.

As concrete examples of phosphoric acid to be used in this invention, condensed phosphoric acids such as diphosphoric acid (pyrophosphoric acid), tripolyphosphoric acid, tetrapolyphosphoric acid, and other polyphosphoric acids, trimetaphosphoric acid, tetrametaphosphoric acid, hexametaphosphoric acid, and other metaphosphoric acids, and strong phosphoric acid may be cited besides orthophosphoric acid. The salts of orthophosphoric acid, diphosphoric acid, tripolyphosphoric acid, tetrapolyphosphoric acid, trimetaphosphoric acid, hexametaphosphoric acid, and other metaphosphoric acids are excellent in terms of the behavior of solubility and are used particularly advantageously.

The basic amino acids which are usable in this invention include natural basic amino acids such as lysine, arginine, and ornithine and basic derivatives thereof and basic derivatives of neutral amino acids as well, for example. One member or a mixture of two or more members selected from the group of basic amino acids enumerated above may be suitably used. To be more specific, natural basic amino acids such as lysine, arginine, and ornithine; amides and esters of amino acid such as methionine, tryptophan, and threonine; and basic derivatives such as basic amino acid-containing peptides are fit for use herein.

The alkaline earth metals which are used in this invention include magnesium, calcium, strontium, and barium, for example. From the viewpoint of biologically safe acceptability, the salts of magnesium and calcium are advantageously usable.

The phosphoric acid-amino acid complex salt of the present invention is a complex salt which is obtained in the form of precipitated crystals when a basic amino acid, an alkaline earth metal, and phosphoric acid are caused to coexist at relatively high concentrations in an aqueous solution under a neutral to alkaline condition. It is broadly divided into four types of phosphoric acid-amino acid complex salt by the presence or absence of condensation of phosphoric acid, the form of condensation, and, in the case of orthophosphoric acid, by the equivalent weight ratio of the basic amino acid and the alkaline earth metal.

The first type of the complex salt is an amino acid complex salt which is composed of three equivalent weights of phosphoric acid which is orthophosphoric acid, one equivalent weight of a basic amino acid, and two equivalent weights of an alkaline earth metal and the second type of the complex salt is a phosphoric acid-amino acid complex salt which is composed of 3.0 equivalent weights of orthophosphoric acid, 0.05 to 0.8 equivalent weights of a basic amino acid, 2.2 to 2.94 equivalent weights of an alkaline earth metal, and 0 to 0.3 equivalent weights of a hydrogen residue. As an alkaline earth metal for the first type and the second type of phosphoric acid-amino acid complex salt, though the salts severally of magnesium and calcium offer a proper choice, the salt solely of magnesium and the mixed salt of magnesium and calcium offer a particularly appropriate choice. The third type of phosphoric acid-amino acid complex salt is a phosphoric acid-amino acid complex salt which uses condensed phosphoric acid as a phosphoric acid and is composed of condensed phosphoric acid, a basic amino acid, an alkaline earth metal, and hydrogen ion at an equivalent weight ratio of 100:2 to 30:70 to 98:0 to 20. The fourth type of phosphoric acid-amino acid complex salt is a phosphoric acid-amino acid complex salt which uses metaphosphoric acid as a phosphoric acid and is composed of metaphosphoric acid, a basic amino acid, an alkaline earth metal, and hydrogen ion at an equivalent weight ratio of 100:2 to 30:70 to 98:0 to 20. As an alkaline earth metal for the third type and the fourth type of phosphoric acid-amino acid complex salt, though the salts severally of magnesium and calcium offer a proper choice, the salt solely of calcium and the mixed salt of magnesium and calcium offer a particularly appropriate choice.

The method for the production of the first type and the second type of phosphoric acid-amino acid complex salt using orthophosphoric acid as phosphoric acid is not critical when the products are insoluble in a neutral to alkaline aqueous solution and soluble in an acidic aqueous solution. The following four methods are available for the production.

The first method fulfills the production by dispersing the secondary phosphate of the alkaline earth metal in a basic aqueous solution of an excess amount of the basic amino acid, heating the resultant dispersion, and washing the precipitate consequently formed in the dispersion. As a concrete example of this method, a method which comprises adding such an alkaline earth metal secondary phosphate as magnesium hydrogen phosphate to an excess amount of a basic concentrated aqueous solution of a basic amino acid prepared as by a treatment with an ion-exchange resin and heating and stirring them until necessary mixture may be cited. The alkaline earth metal secondary phosphate in the mixed solution undergoes gradual extinction and the phosphoric acid-amino acid complex salt is produced in the form of a precipitate. When the precipitate is isolated by means of solid-liquid separation, washed with water to expel the excess basic amino acid, and then dried, an amino acid complex salt which is composed of three equivalent weights of orthophosphoric acid, one equivalent weight of the basic amino acid, and two equivalent weights of the alkaline earth metal with respect to the aforementioned general formula (1) or a phosphoric acid-amino acid complex salt composition having the complex salt as a main component thereof is obtained. The water of hydration can be obtained in a wide range of from anhydride to decahydrate. Under normal conditions, the product is obtained in the form of a monohydrate or a dihydrate.

The second method fulfills the production by mixing a neutral aqueous solution of the alkaline earth metal and either orthophosphoric acid or an alkali metal salt of the orthophos-phoric acid at an equivalent weight ratio of 2.9 to 2.0:3.0 in a basic aqueous solution of an excess amount of the basic amino acid and washing the precipitate consequently formed. As a concrete example of this method, a method which comprises adding three equivalent weights of orthophosphoric acid and/or an alkali metal salt of the orthophosphoric acid to not less than three equivalent weights of a basic concentrated aqueous solution of the basic amino acid thereby forming a high-concentration tertiary phosphate solution, then adding 2.9 to 2.0 equivalent weights of a concentrated aqueous solution of such a neutral salt of an alkaline earth metal as magnesium chloride or magnesium sulfate, stirring them until necessary mixture, isolating the consequently formed precipitate by means of solid-liquid separation, and washing the isolated precipitate with water thereby expelling the excess basic amino acid, and drying the washed precipitate may be cited. By this method is obtained a phosphoric acid-amino acid complex salt represented by the afore-mentioned general formula (1). By this method, phosphoric acid-amino acid complex salt compositions having the first type and the second type of complex salt mentioned above respectively as main components thereof are obtained, depending on the equivalent weight ratio of the alkaline earth metal salt and the phosphoric acid, the speed of addition, and the kind of seed crystals during the course of addition.

The phosphoric acid-amino acid complex salt composition having the first type of the complex salt as a main component thereof is obtained when the amount of the neutral salt solution of the alkaline earth metal to be added is close to two equivalent weights based on three equivalent weights of the orthophosphoric acid and/or the alkali metal salt of the ortho-phosphoric acid and the neutral salt solution of the alkaline earth metal is gradually added in the presence of the first type of the complex salt as seed crystals. Conversely, the second type of the complex salt or the phosphoric acid-amino acid complex salt composition having the complex salt as a main component thereof is obtained when the amount of the neutral salt solution of the alkaline earth metal to be added is close to 2.8 equivalent weights based on 3.0 equivalent weights of the ortho-phosphoric acid and the addition is made abruptly. Otherwise, the production is attained with the amount of the alkaline earth metal in the range of from 2.94 to 2.0 equivalent weights. By this method, phosphoric acid-amino acid complex salts of the aforementioned general formula (1) having a varied in the range of from 0.05 to 1, b varied in the range of from 1 to 1.47, c varied in the range of from 0 to 0.3, and n varied in the range of from 0 to 10 can be obtained.

The third method implements the production by adding 2.9 to 2.0 equivalent weights of the hydroxide of an alkaline earth metal and/or the oxide of an alkaline earth metal to a primary phosphate solution of the basic amino acid, mixing them, and washing the precipitate consequently formed. As a concrete example of this method, a method which comprises mixing 0.7 to 1.4 equivalent weights of a basic concentrated aqueous solution of the basic amino acid and three equivalent weights of ortho-phosphoric acid until necessary neutralization thereby forming a concentrated aqueous solution having the primary phosphate of the basic amino acid as a main component thereof, adding to this solution 2.9 to 2.0 equivalent weights of the hydroxide of such an alkaline earth metal as magnesium hydroxide or calcium hydroxide and/or the oxide of such an alkaline earth metal as magnesium oxide or calcium oxide in the form of an aqueous dispersion, and mixing them may be cited. The hydroxide of the alkaline earth metal and/or the oxide of the alkaline earth metal so added undergoes gradual extinction and a phosphoric acid-amino acid complex salt is formed as a precipitate. This phosphoric acid-amino acid complex salt is ultimately obtained by isolating this precipitate by means of solid-liquid separation, washing the isolated precipitate with water until expulsion of the excess basic amino acid, and drying the residue of the washing. By this method is obtained the phosphoric acid-amino acid complex salt represented by the aforementioned general formula (1). By this method, phosphoric acid-amino acid complex salt compositions having the first type and the second type of complex salt mentioned above respectively as main components thereof are obtained, depending on the equivalent weight ratio of the alkaline earth metal salt and the phosphoric acid and the kind of seed crystals at the time of addition.

Similarly in the third method, the first type of the complex salt or the phosphoric acid-amino acid complex salt composition having the complex salt as a main component thereof is obtained when the amount of the hydroxide of the alkaline earth metal and/or the oxide of the alkaline earth metal is close to two equivalent weights relative to three equivalent weights of the orthophosphoric acid and the neutral salt solution of the alkaline earth metal is gradually added in the presence of the first type of complex salt as seed crystals. Conversely, the second type of the complex salt or the phosphoric acid-amino acid complex salt composition having the complex salt as a main component thereof is obtained when the amount of the neutral salt solution of the alkaline earth metal to be added is close to 2.8 equivalent weights relative to 3.0 equivalent weights of the orthophosphoric acid and the addition is made in the presence of the second type of the complex salt as seed crystals. By adding to the aqueous solution of the primary phosphate of the basic amino acid 2.94 to 2.0 equivalent weights of the hydroxide of the alkaline earth metal and/or the oxide of the alkaline earth metal relative to three equivalent weights of the ortho-phosphoric acid, mixing them, and washing the consequently formed precipitate, phosphoric acid-amino acid complex salts of the aforementioned general formula (1) having a varied in the range of from 0.05 to 1, b varied in the range of from 1 to 1.47, c varied in the range of from 0 to 0.3, and n varied in the range of from 0 to 10 can be obtained.

The fourth method accomplishes the production by mixing a basic aqueous solution of the basic amino acid and orthophos-phoric acid at an equivalent weight ratio of 0.05 to 0.8 vs. 3.0 thereby forming a neutralized solution, adding to the neutralized solution 2.94 to 2.2 equivalent weights of the hydroxide of an alkaline earth metal, mixing them, and heating and drying the resultant mixture. As a concrete example of this method, a method which comprises mixing 0.05 to 0.8 equivalent weights of the basic concentrated aqueous solution of the basic amino acid and 3.0 equivalent weights of the orthophosphoric acid until neutralization thereby forming a mixed concentrated aqueous solution of the primary phosphate and the orthophosphoric acid, adding to this solution 2.94 to 2.2 equivalent weights of the hydroxide of such an alkaline earth metal as magnesium hydroxide or calcium hydroxide in the form of an aqueous dispersion, and mixing them may be cited. The added hydroxide of the alkaline earth metal undergoes gradual extinction and a phosphoric acid-amino acid complex salt is formed as a precipitate. A phosphoric acid-amino acid complex salt represented by the aforementioned general formula (1) is obtained by drying the precipitate in its unmodified form. By this method, the second type of the complex salt or the phosphoric acid-amino acid complex salt composition having the complex salt as a main component is obtained. By mixing three equivalent weights of orthophosphoric acid with 0.05 to 0.8 equivalent weights of the basic amino acid in the form of a basic aqueous solution and 2.94 to 2.2 equivalent weights of the hydroxide of an alkaline earth metal and/or the oxide of an alkaline earth metal and then heating and drying the resultant mixture, phosphoric acid-amino acid complex salts of the aforementioned general formula (1) having a varied in the range of from 0.05 to 0.8, b varied in the range of from 1.1 to 1.47, c varied in the range of from 0 to 0.3, and n varied in the range of from 0 to 10 can be obtained.

These four methods have in common the fact that a basic concentrated aqueous solution of a basic amino acid is used as a raw material and an amino acid complex salt is formed in consequence of a reaction using the basic amino acid at a relatively high concentration. In this invention, the concentration of the basic amino acid is appropriate in the range of 10 to 60 parts by weight based on 100 parts by weight of the total amount of water present in the reaction system in the case of the second method which selects the highest concentration and in the range of 3 to 20 parts by weight based on 100 parts by weight of the total amount of water in the case of the fourth method which selects the lowest concentration.

These four methods may be used as suitably combined. As concrete examples of the combination, a method which comprises adding a concentrated aqueous solution of a neutral salt of the orthophosphoric acid and/or an alkali metal salt of the orthophosphoric acid in a suitable amount to the reaction solution having a phosphoric acid-amino acid complex salt formed in the form of a precipitate by the first method described above, stirring them for necessary mixture, and heating the resultant mixture thereby causing the neutral salt to react with the excess amount of the basic amino acid still remaining in the reaction solution and a method which comprises adding the hydroxide of an alkaline earth metal in a suitable amount to the reaction solution having a phosphoric acid-amino acid complex salt formed in the form of a precipitate by the second method described above thereby causing the hydroxide to react with the excess amounts of the basic amino acid and the phosphoric acid still remaining in the reaction solution may be cited. The phosphoric acid-amino acid complex salts which are obtained in these methods are mixtures of the first type of complex salt and the second type of complex salt mentioned above. These methods of production and the reaction conditions involved therein affect the ratio of combination of such mixtures.

The method for the production of the third type and the fourth type of phosphoric acid-amino acid complex salt using condensed phosphoric acid and metaphosphoric acid severally as phosphoric acid is not critical when the products are insoluble in a neutral to alkaline aqueous solution and soluble in an acidic aqueous solution. The method is substantially equal to the method for the production of complex salt using ortho-phosphoric acid except that condensed phosphoric acid and metaphosphoric acid are respectively used as phosphoric acid. The following three methods offer an appropriate choice.

The first method fulfills the production by adding to the basic aqueous solution resulting from adding the phosphoric acid and/or an alkali metal salt of the phosphoric acid to a basic aqueous solution of an excess amount of the basic amino acid 70 to 130 equivalent weights, based on 100 equivalent weights of the phosphoric acid, of a neutral aqueous solution of an alkaline earth metal salt, washing the precipitate consequently formed, and drying the washed precipitate. As a concrete example of the method, a method which comprises adding 70 to 130 equivalent weights of a neutral aqueous solution of such an alkaline earth metal as magnesium chloride, magnesium sulfate, or calcium chloride to 100 equivalent weights of phosphoric acid selected from among diphosphoric acid (pyrophosphoric acid), tripoly-phosphoric acid, tetrapolyphosphoric acid, and other polyphos-phoric acids, trimetaphosphoric acid, tetrametaphosphoric acid, hexametaphosphoric acid, and other metaphosphoric acids and/or the alkali metal salt of the phosphoric acid in a basic aqueous solution of an excess amount of the basic amino acid prepared as by the treatment with an ion-exchange resin, allowing them to react and produce a precipitate, washing this precipitate with a large volume of water, and drying the washed precipitate may be cited. By this method, a phosphoric acid-amino acid complex salt represented by the general formula (2) or the general formula (3) mentioned above or a complex salt composition having the complex salt as a main component thereof is obtained.

The second method attains the production of a complex salt by mixing 100 equivalent weights of the phosphoric acid with 2 to 50 equivalent weights of the basic amino acid in the form of a basic aqueous solution and 70 to 130 equivalent weights of the hydroxide of an alkaline earth metal and/or the oxide of an alkaline earth metal thereby giving rise to a precipitate, and washing the precipitate. As a concrete example of this method, a method which comprises mixing 2 to 50 equivalent weights of a basic aqueous solution of an excess amount of the basic amino acid prepared as by the treatment with an ion-exchange resin with 100 equivalent weights of phosphoric acid selected from among diphosphoric acid (pyrophosphoric acid), tripoly-phosphoric acid, tetrapolyphosphoric acid, and other polyphosphoric acids, tri-metaphosphoric acid, tetrametaphosphoric acid, hexametaphosphoric acid, and other metaphosphoric acids and 70 to 130 equivalent weights of the hydroxide and/or the oxide of such an alkaline earth metal as calcium hydroxide, magnesium hydroxide, calcium oxide, or magnesium oxide, causing them to react and give rise to a precipitate, washing the precipitate, and the drying the washed precipitate may be cited. By this method, a phosphoric acid-amino acid complex salt represented by the general formula (2) or the general formula (3) mentioned above or a complex salt composition having the complex salt as a main component thereof is obtained.

The third method implements the production of a complex salt by mixing 100 equivalent weights of the phosphoric acid with 2 to 30 equivalent weights of the basic amino acid in the form of a basic aqueous solution and 70 to 130 equivalent weights of the oxide of an alkaline earth metal and/or the oxide of an alkaline earth metal and then heating and drying the resultant mixture. As a concrete example of this method, a method which comprises mixing 2 to 50 equivalent weights of a basic aqueous solution of an excess amount of the basic amino acid prepared as by the treatment with an ion-exchange resin with 100 equivalent weights of phosphoric acid selected from among diphosphoric acid (pyrophosphoric acid), tripolyphosphoric acid, tetrapolyphosphoric acid, and other polyphosphoric acids, trimetaphosphoric acid, tetrametaphosphoric acid, hexametaphosphoric acid, and other metaphosphoric acids and 70 to 130 equivalent weights of the hydroxide and/or the oxide of such an alkaline earth metal as calcium hydroxide, magnesium hydroxide, calcium oxide, or magnesium oxide and heating and mixing the resultant mixture may be cited. By this method, a phosphoric acid-amino acid complex salt represented by the general formula (2) or the general formula (3) mentioned above or a complex salt composition having the complex salt as a main component thereof is obtained. By mixing 100 equivalent weights of at least one substance selected from among condensed phosphoric acid, metaphosphoric acid, alkali metal salts of condensed phosphoric acid, and alkali metal salts of metaphosphoric acid with 70 to 130 equivalent weights of a neutral aqueous solution of an alkaline earth metal in a basic aqueous solution of an excess amount of the basic amino acid and then washing the precipitate consequently formed, phosphoric acid-amino acid complex salts of the aforementioned general formula (2) or (3) having a, b, and c varied in the respective ranges of 0.02 to 0.3, 0.35 to 0.49, and 0 to 0.2 and n varied in the range of 0 to 20 can be obtained.

The third type and the fourth type of complex salt of this invention may be prepared independently of each other. A method which obtains a mixed composition of the third type and the fourth type of complex salt by using condensed phosphoric acid and metaphosphoric acid as the raw materials either at the same time or as mixed in advance can be adopted as an appropriate method. By mixing 100 equivalent weights of condensed phosphoric acid and/or metaphosphoric acid with 2 to 50 equivalent weights of the basic amino acid in the form of a basic aqueous solution and 70 to 130 equivalent weights of the hydroxide of an alkaline earth metal and/or the oxide of an alkaline earth metal and then washing the consequently formed precipitate, phosphoric acid-amino acid complex salts of the aforementioned general formula (2) or (3) having a, b, and c varied in the respective ranges of 0.02 to 0.3, 0.35 to 0.49, and 0 to 0.2 and n varied in the range of 0 to 20 can be obtained.

Besides the method for preparing the first type and the second type of complex salt and the third type and the fourth type of complex salt independently of each other, a method for obtaining a mixed composition of the first through fourth types of complex salt by using the relevant species of phosphoric acid as raw materials either at the same time or as mixed in advance can be adopted. A method which forms the third type and/or the fourth type of complex salt by preparing a reaction solution having the first type and the second type of complex salt formed in advance therein and adding condensed phosphoric acid and/or metaphosphoric acid and an alkaline earth metal to the reaction solution and a method which obtains a mixed composition of the first through fourth types of complex salt by preparing a reaction solution having the third type and the fourth type of complex salt composition formed in advance therein and adding orthophosphoric acid and an alkaline earth metal to the reaction solution thereby forming the first type and/or the second type of complex salt can be adopted as appropriate methods. To be more specific, by mixing 100 equivalent weights of condensed phosphoric acid and/or metaphosphoric acid with 2 to 30 equivalent weights of the basic amino acid in the for of a basic aqueous solution thereby forming a solution, mixing this solution with 70 to 130 equivalent weights of the hydroxide of an alkaline earth metal and/or the oxide of an alkaline earth metal, and then heating and drying the resultant mixture, phosphoric acid-amino acid complex salts of the aforementioned general formula (2) or (3) having a, b, and c varied in the respective ranges of 0.02 to 0.3, 0.35 to 0.49, and 0 to 0.2 and n varied in the range of 0 to 20 can be obtained.

The four species of complex salt mentioned above can be identified distinctly from one another by the degree of condensa-tion of phosphoric acid, the ratio of combination of the basic amino acid and the alkaline earth metal, and the powder X-ray diffraction analysis as well. In the powder X-ray diffraction spectrum using a copper K $\alpha$ ray, the first type of complex salt shows main peaks each with $2\Theta$ at about 3.7°, about 7.4°, about 18.5°, about 18.8°, about 20.7°, about 22.2°, about 29.7°, and about 32.3° and the second type of complex salt shows main peaks at about 6.0° to about 6.5°, about 7.4° to about 7.7°, about 15.6°, about 28.2°, and about 32.5°. The third type and the fourth type of complex salt show no clear peak. They show a slight bulge or a very small peak on the base line of $2\Theta$ in the range of about 25° to 35°.

In the four species of complex salt mentioned above, the first type of complex salt, when using lysine as a basic amino acid and magnesium as an alkaline earth metal, shows very sharp peaks in the powder X-ray diffraction mentioned above. This fact indicates that it is a complex salt having highly satisfactory crystallinity. By the analysis for composition, this complex salt is found to have a composition of 1 mol of orthophosphoric acid, 1 mol of lysine, and 1 mol of magnesium and a water of hydration of 2 mols under normal dry condition, though this water of hydration is variable with the condition of dryness. The complex salt of this composition has never been known to exist.

In the four species of complex salt mentioned above, as regards the second type of complex salt using lysine as a basic amino acid and magnesium as an alkaline earth metal, the presence of the stablest crystal composition has been newly discovered. It has been observed that when the second type of complex salt is heat-treated for a long time in a basic aqueous solution containing lysine at a relatively high concentration, the powder X-ray diffraction of the heat-treated complex salt shows decisively sharp peaks as compared with that of the complex salt prior to the heat treatment. It has been also brought to light that the heat treatment mentioned above produces the same result on several samples of the second type of complex salt containing lysine, phosphoric acid, and magnesium at diverse concentrations and that the heat-treated samples contain lysine, phosphoric acid, and magnesium at invariable concentrations. This fact indicates the presence of the stablest crystal composition in the second type of complex salt. The crystal composition has lysine as a basic amino acid, magnesium as a basic amino acid, and orthophosphoric acid as phosphoric acid, contains lysine hydrogen cation at a concentration in the range of 0.21 to 0.25 mol, magnesium at a concentration in the range of 1.325 to 1.395 mol, and hydrogen ion in the range of 0 to 0.1 mol per mol of ortho-phosphoric acid, and has water of hydration of 0 to 5 mols. It has been also found that the water of hydration readily varies with the condition of dryness. The existence of a complex salt having this composition has never been known.

Though the four species of complex salt manifest no solubility to neutral to alkaline water, the basic amino acid components thereof are found to differ from one another in behavior of solution. Specifically, the first type of complex salt, when dispersed in neutral water, disposes the basic amino acid component thereof to be exclusively dissolved out gradually, whereas the second through fourth types of complex salt very rarely allow their basic amino acid components to be dissolved out in neutral water.

In the case of the second through fourth types of complex salt mentioned above or the phosphoric acid-amino acid complex salt compositions having the complex salts as their respective main components, therefore, the ultimately produced crystalline powders of the complex salt compositions, even when used in their unmodified form, are possessed of the quality of manifesting insolubility in neutral to alkaline water and solubility in acidic water and can be utilized as additive compositions in the powdery feeds for ruminant mammals which are stable in the rumen and capable of releasing the basic amino acid in the fourth compartment of the stomach and the subsequent digestive organs.

In contrast, in the case of the first type of complex salt mentioned above or the phosphoric acid-amino acid complex salt composition having the complex salt as a main component thereof, it is more appropriate to mold the complex salt or the composition in the form of granules of a suitable particle diameter and consequently decrease the capacity of dissolving out the basic amino acid component into neutral or alkaline water than to use the complex salt or the composition in its unmodified form. Even in this case, since the phosphoric acid-amino acid complex salt of this invention is possessed of the quality of dissolving out in acidic water and the granulated product thereof the quality of manifesting solubility in the fourth compartment of the stomach without reference to the composition thereof, it can be utilized as an additive composition in a powdery feed for ruminant mammals which is stable in the rumen and capable of releasing the basic amino acid in the fourth compartment of the stomach and the subsequent digestive organs.

In this invention, the granules of the phosphoric acid-amino acid complex salt can be used particularly advantageously when they have a homogeneous granular structure. The expression "homogeneous granules" as used in this invention refers to such granules that the fragments which the granules happen to form in diameters in the approximate range of 1 to 2 mm retain a compo-sition invariable among the fragments. The minimum particle diameters of the fragments into which the granules are broken by ruminant mastication fall in the approximate range of 1 to 2 mm. When the fragments of granules measuring approximately 1 to 2 mm in particle diameter have a uniform composition, therefore, the granules which have undergone the ruminant mastication ought to have a uniform composition. When the granules are blended with other feed components and then tableted, the ability of the granules to dissolve out the basic amino acid component thereof is not affected noticeably by the impact possibly exerted thereon meanwhile.

For the granulation of the phosphoric acid-amino acid complex salt of this invention, any of the methods in popular use for granulation in general without any restriction so long as the homogeneity mentioned above is retained. As concrete examples of the method which is advantageously used, a method which comprises mixing the complex salt with a suitable binder and then granulating the resultant mixture by such a granulating technique as the extrusion granulation technique, rolling granulation technique, compression granulation technique, or melt spraying granulation technique, a method which comprises converting the complex salt into a slurry and spray drying the slurry, and a method which comprises converting the complex salt into a powder, blending this powder with a binder, and granulating the resultant mixture by the fluidized-bed granulation technique or agitation granulation technique may be cited.

As the binder, in the case of the phosphoric acid-amino acid complex salt compositions having the second through fourth types of complex salts mentioned above as respective main components, any of the binders in popular use can be adopted without any particular restriction. As concrete examples of the binder, water-soluble binders including water-soluble polysaccharides such as starch, salts of carboxymethyl cellulose, alginates, methyl cellulose, ethyl cellulose, hydroxypropyl cellulose, and salts of starch glycolic acid; water-soluble proteins such as casein sodium, gelatin, and soybean protein, saccharides such as molasses, milk sugar, and dextrin, and synthetic macromolecules such as polymethacrylates, polyvinyl alcohols, and polyvinyl pyrrolidone and hydrophobic binders including natural waxes such as shellac resin, rosin, beeswax, and paraffin waxes, higher fatty acids such as cetanol and stearic acid, oil- and fat-related substances such as metal salts of higher fatty acids, animal and plant oils and fats, and cured animal and plant oils and fats, nonionic surfactants such as glycerin monostearate, and semisynthetic resins and synthetic macromolecules such as acetyl cellulose, polyvinyl acetate, ester gums, and cumarone resin may be cited. In the case of the phosphoric acid-amino acid complex salt having the first type of complex salt mentioned above as a main component thereof, it is appropriate to use any of the hydrophobic binders mentioned above. The natural waxes and the oil- and fat-related substances mentioned above offer a still more appropriate choice.

The ratio of combination of the phosphoric acid-amino acid complex salt and the binder in the formation of granules varies with the kind of binder to be used. In the case of the phosphoric acid-amino acid complex salt having the first type of complex salt as a main component thereof, the ratio properly is in the range of 30 to 350 parts by weight of the binder to 100 parts by weight of the phosphoric acid-amino acid complex salt. In the case of the phosphoric acid-amino acid complex salt having any of the second through fourth types of complex salt as a main component, the ratio appropriately is in the range of 0.1 to 50 parts by weight of the binder to 100 parts by weight of the phosphoric acid-amino acid complex salt.

The particle diameter of the granules containing the phosphoric acid-amino acid complex salt of this invention is not particularly critical. The granules having an average particle diameter of not more than about 5 mm prove appropriate in that the feed using the granules suffers only indistinct dispersion of quality and those having an average particle in the range of 2 to 0.2 mm prove particularly advantageous in that these granules facilitate the work of mixing the granules with other feed components.

The granules containing the phosphoric acid-amino acid complex salt of this invention, in the process of preparation thereof, may incorporate therein other additives besides the amino acid complex salt and the binder for the purpose of adjusting the specific gravity, augmenting the strength of granules, enhancing the solubility in the fourth compartment of the stomach, and improving the processibility during the fabrica-tion of granules. These additives are selected from among powdery or waxy substances. As concrete examples of the additives which are appropriately used therefor, inorganic substances such as carbonates, phosphates, and hydroxides of alkaline earth metals, talc, bentonite, clay, and finely divided silica and organic substances such as paraffin waxes, poly-ethylene powder, pulp powder, cellulose powder, and chitosan may be cited.

The granules containing the phosphoric acid-amino acid complex salt of this invention, during the course of preparation, is allowed to have other biologically active substances uniformly dispersed therein on the condition that their presence therein avoids impairing the protectiveness of the phosphoric acid-amino acid complex salt in the rumen and the solubility thereof in the fourth compartment of the stomach. The biologically active substances which fit this purpose include various well-known nutritious substances and medicines such as, for example, amino acids and derivatives thereof, hydroxy homologous compounds of amino acids, vitamins, and veterinary medicines. One member or a mixture of two or more members selected from the group of substances cited above may be suitably used.

As concrete examples of the biologically active substance, amino acids such as methionine, tryptophan, and threonine; amino acid derivatives such as calcium salts of N-acylamino acid and N-hydroxymethyl methionine; hydroxy homologous compounds of amino acids such as 2-hydroxy-4-methyl mercaptobutyric acid and salts thereof; starch, fatty acids, and metal salts of fatty acids as calory sources; vitamins and substances possessed of functions similar thereto such as vitamin A, vitamin A acetate, vitamin A palmitate, vitamin B series, thiamine, thiamine hydrochloride, riboflavin, nicotinic acid, nicotinic acid amide, calcium pantothenate, pyridoxine hydrochloride, choline chloride, cyanocobalamine, biotin, folic acid, p-aminobenzoic acid, vitamin $D_2$, vitamin $D_3$, and vitamin E; antibiotic substances of the tetracycline type, aminoglycoside type, macrolide type, and poly-ether type, parasiticides such as negphon, vermifuges such as piperazine, and hormones such as estrogen, stilbestrol, hexe-strol, goitrogen, and growth hormone may be cited.

EXAMPLES

Now, this invention will be described more specifically below with reference to working examples and comparative experiments. The scope of this invention is not limited to these working examples.

The amount of amino acid contained as a biologically active substance and the amount thereof dissolved out were determined by liquid chromatography, the water content by the method of weight loss by drying (three hours' standing in a vacuum at 120° C.), and the calcium, magnesium, and phosphorus contents by the IPC (inductive plasma coupling) emission spectral analysis.

Solubility into pure water

In an Erlenmeyer flask 200 ml in inner volume, 1.00 g of a prepared sample was placed and 100 ml of purified water was added thereto and the resultant aqueous solution was subjected to an ultrasonic treatment at normal room temperature for 10 minutes. The solution was analyzed for the basic amino acid to determine the solubility of the sample into the purified water.

Protectiveness against gastric fluid in first compartment of the stomach

In an Erlenmeyer flask 300 ml in inner volume, about 0.5 g of a prepared sample was placed, 200 ml of McDougall buffer solution* equivalent to the gastric fluid in the first compart-ment of the stomach was added to the sample, and the resultant mixture was shaken at 39° C. for 24 hours. After the shaking was completed, the shaken mixture was analyzed for the basic amino acid dissolved out therein to determine through calculation the protectiveness against the gastric fluid in the first compartment of the stomach.

* McDougall buffer solution: A buffer solution having the following reagents dissolved in 1000 ml of water.

| | |
|---|---|
| Sodium hydrogen carbonate | 7.43 g |
| Disodium phosphate dodecahydrate | 7.00 g |
| Sodium chloride | 0.34 g |
| Potassium chloride | 0.43 g |
| Magnesium chloride hexahydrate | 0.10 g |
| Calcium chloride | 0.05 g |

Solubility into solution equivalent to gastric fluid in fourth compartment of the stomach In an erlenmeyer flask 300 ml in inner volume, about 0.5 g of a prepared sample was placed, 200 ml of acetic acid-phosphoric acid buffer solution* equivalent to the gastric fluid in the fourth compartment of the stomach was added to the sample, and the resultant mixture was shaken at 39° C. for one hour. After the shaking was completed, the shaken sample was analyzed for the basic amino acid dissolved out therein to determine the solubility of the sample into the solution equivalent to the gastric fluid in the fourth compartment of the stomach.

* Acetic acid-phosphoric acid buffer solution: A buffer solution obtained by dissolving the following reagents in 1000 ml of water and neutralizing the resultant aqueous solution with hydrochloric acid to pH 2.2.

| | |
|---|---|
| Sodium dihydrogen phosphate dihydrate | 1.95 g |
| Sodium acetate trihydrate | 3.40 g |

Example 1

When 1300 g of an aqueous L-lysine base solution (45 wt % in concentration) and 174.3 g of magnesium secondary phosphate.-trihydrate added thereto were heated and stirred at 80° C. for three hours, the granular crystals of magnesium secondary phosphate.trihydrate vanished and minute crystals occurred in large quantity. The crystals thus formed were separated by filtration, washed with 1000 ml of water, and then dried at 60° C. under a reduced pressure to obtain 285 g of a white crystalline powder. When 1 g of the white powder was placed in 100 ml of purified water and the buffer solution equivalent to the gastric fluid in the first compartment of the stomach and stirred therein, it showed no sign of solution therein. Though the white powder had one molecule of water of hydration, the water of hydration could be varied in the range of 0 to 10 molecules depending on the drying condition. Under the normal drying condition, the water of hydration or one or two molecules. In the following working examples, the relevant complex salts could be obtained with as wide a range of hydration as in the present example.

Example 2

To a liquid obtained by mixing 4386 g of an aqueous L-lysine base solution (20 wt % in concentration) with 231 g of phosphoric acid (85% in concentration) until neutralization, a solution of 493 g of magnesium sulfate.heptahydrate in 1000 ml of water was added at once. The gel precipitate which occurred consequently was separated by filtration, washed with 12000 ml of water, and then dried at 60° C. under a reduced pressure to obtain 280 g of a white powder. When 1 g of the white powder was placed in 100 ml of purified water and the buffer solution equivalent to the gastric fluid in the first compartment of the stomach and stirred therein, it showed no sign of solution therein.

Example 3

When a solution obtained by dispersing 291.7 g of magnesium hydroxide in 1000 ml of water was added to and mixed with a liquid obtained by mixing 650 g of an aqueous L-lysine base solution (45 wt % in concentration) with 461.2 g of phosphoric acid (85% in concentration) until neutralization, an exothermic reaction ensued to produce a white solid substance. This white solid substance was heated at 95° C. for three hours and then placed in 3000 ml of water and thoroughly disintegrated therein. The solid phase consequently formed was separated by filtration, washed with 3000 ml of water, and then dried at 60° C. under a reduced pressure to obtain 750 g of a white powder. When 1 g of the white powder was placed in 100 ml of purified water and the buffer solution equivalent to the gastric fluid in the first compartment of the stomach and stirred therein, it showed no sign of solution therein.

Example 4

When a liquid obtained by mixing 311 g of an aqueous L-lysine base solution (47 wt % in concentration) with 461.2 g of phosphoric acid (85% in concentration) until neutralization and a solution obtained by dispersing 291.7 g of magnesium hydroxide with 700 ml of water were homogeneously mixed, an exothermic reaction ensued to produce a white solid substance. This white solid substance was heated at 90° C. for three hours, then crushed, and dried at 60° C. under a reduced pressure to obtain 750 g of a white powder. When 1 g of the white powder was placed in 100 ml of purified water and the buffer solution equivalent to the gastric fluid in the first compartment of the stomach and stirred therein, it showed no sign of solution therein.

Example 5

When 20 g of the white crystalline powder obtained in Example 1 was added to a liquid obtained by mixing 4386 g of an aqueous L-lysine base solution (20 wt % in concentration) with 231 g of phosphoric acid (85% in concentration) until neutralization and a solution of 407 g of magnesium chloride.hexahydrate in 500 ml of water was gradually added thereto piecemeal, minute crystals occurred. The crystals thus obtained were separated by filtration, washed with 3000 ml of water, and then dried at 60° C. under a reduced pressure to obtain 573 g of a white crystalline powder. When 1 g of the white powder was placed in 100 ml of purified water and the buffer solution equivalent to the gastric fluid in the first compartment of the stomach and stirred therein, it showed no sign of solution therein.

Example 6

When 87.2 g of magnesium secondary phosphate.trihydrate was added to 730 g of an aqueous L-lysine base solution (40 wt % in concentration) and they were then heated and stirred at 80° C. for three hours, the granular crystals of magnesium secondary phosphate.trihydrate vanished and minute crystals occurred. When 46.1 g of phosphoric acid (85% in concentration) was gradually added as cooled to the resultant mixed solution and then a solution of 98.6 g of magnesium sulfate.heptahydrate in 150 ml of water was added thereto at once, the resultant mixed solution was converted into a viscous crystalline slurry. The crystals thus obtained were separated by filtration, washed with 1300 ml of water, and then dried at 60° C. under a reduced pressure to obtain 198 g of a white crystalline powder. When 1 g of the white powder was placed in 100 ml of purified water and the buffer solution equivalent to the gastric fluid in the first compartment of the stomach and stirred therein, it showed no sign of solution therein.

Example 7

A solution of 610 g of magnesium chloride.hexahydrate in 1000 ml of water was added at once to a liquid obtained by mixing 4873 g of an aqueous L-lysine base solution (30 wt % in concentration) with 461 g of phosphoric acid (85% in concentra-tion) until neutralization. The viscous mixture which was formed consequently and a solution having 93.3 g of magnesium hydroxide thoroughly dispersed in 700 ml of water were homogeneously mixed and the resultant homogeneous mixture was left standing over-night to obtain a white precipitate. This precipitate was separated by filtration, washed with 7000 ml of water, and then dried at 60° C. under a reduced pressure to obtain 980 g of a white powder. When 1 g of the white powder was placed in 100 ml of purified water and the solution equivalent to the gastric fluid in the first compartment of the stomach and stirred therein, it showed no sign of solution therein.

Example 8

The crystalline powders and white powders obtained in Examples 1 through 7 were tested for water content and lysine content by the Karl Fischer technique and the weight loss by drying technique (three hours' standing at 120° C. under a vacuum) and for Mg content and phosphorus content by the IPC (inductive plasma coupling) emission spectral analysis technique. The results are shown in Table 1. The lysin content of a given sample was determined by dissolving the sample in dilute hydro-chloric acid and analyzing the resultant solution by liquid chromatography. The data on the ratio of solution into purified water, the protectiveness against the buffer solution equivalent to the gastric fluid in the first compartment of the stomach, and the solubility in the buffer solution equivalent to the gastric fluid in the fourth compartment of the stomach are shown additionally in Table 1.

Example 9

When a liquid obtained by mixing 650 g of an aqueous L-lysine base solution (45 wt % in concentration) with 461.2 g of phosphoric acid (85% in concentration) until neutralization and a solution having 201.5 g of magnesium oxide dispersed in 600 ml of water were homogeneously mixed, an exothermic reaction ensued to produce a white solid substance. This white solid substance was pulverized, washed with 12000 ml of water, and then dried at 60° C. under a reduced pressure to obtain 650 g of a white powder. When 1 g of the white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concentration, the concentration was found to be 112 mg/dl, indicating that the L-lysine content was 11.2%. When 1.00 g of this white powder was mixed with 100 ml of purified water, the resultant mixture was subjected to an ultrasonic treatment for five minutes, and the supernatant consequently formed was tested for L-lysine concen-tration, the L-lysine concentration was found to be 12 mg/dl. The results indicate that the ratio of solution of L-lysine into purified water was 10.7%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 85% and the ratio of solution to be 100% respectively.

Example 10

When a liquid obtained by mixing 311 g of an aqueous L-lysine base solution (47 wt % in concentration) with 461.2 g of phosphoric acid (85% in concentration) until neutralization and a solution having 233.3 g of magnesium hydroxide and 74.1 g of calcium hydroxide dispersed in 700 ml of water were homogeneously mixed, an exothermic reaction

TABLE 1

| Example | 1 | 2 | 3 | Unit: wt% Numeral in brackets [ ]: equivalent ratio relative to phosphoric acid 4 | 5 | 6 | 7 |
| --- | --- | --- | --- | --- | --- | --- | --- |
| Loss of weight of KF water | 7.3 | 19.3 | 16.4 | 13.7 | 8.4 | 12.5 | 15.5 |
| content in total water | 7.2 | 8.7 | 6.2 | 7.8 | 7.9 | 8.5 | 8.9 |
| content at 120° C. | 7.0 | 19.0 | 16.2 | 13.5 | 8.1 | 12.2 | 15.3 |
| Content other than water | 92.7 | 80.7 | 83.6 | 86.3 | 91.6 | 87.5 | 84.5 |
| Lysine content | 51.1 | 20.0 | 18.5 | 19.5 | 50.4 | 36.5 | 29.8 |
|  | [1.00] | [0.29] | [0.25] | [0.26] | [1.00] | [0.60] | [0.46] |
| Mg content | 8.5 | 15.4 | 16.6 | 16.2 | 8.4 | 11.8 | 13.4 |
|  | [2.01] | [2.65] | [2.68] | [2.50] | [2.00] | [2.37] | [2.53] |
| Phosphorus content (as | 10.8 | 14.8 | 15.8 | 16.5 | 10.7 | 12.7 | 13.5 |
| PO$_4$) [taken as 300] | (33.1) | (45.4) | (48.5) | (50.6) | (32.8) | (39.0) | (41.4) |
|  | [3.00] | [3.00] | [3.00] | [3.00] | [3.00] | [3.00] | [3.00] |
| Ratio of separation by solution into pure water | 84.2% | 13.0% | 35.0% | 48.7% | 86.2% | 55.3% | 38.5% |
| Protectiveness in first compartment of the stomach | 10% | 35% | 55% | 42% | 9% | 40% | 57% |
| Separability in fourth compartment of the stomach | 100% | 100% | 100% | 100% | 100% | 100% | 100 | ensued to produce a white solid substance. This white solid substance was pulverized, washed with 10000 ml of water, and then dried at 60° C. under a reduced pressure to obtain 600 g of a white powder. When 1 g of the white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concentration, the concentration was found to be 65 mg/dl, indicating that the L-lysine content was 6.5%. When 1.00 g of this white powder was mixed with 100 ml of purified water, the resultant mixture was subjected to an ultrasonic treatment for five minutes, and the supernatant consequently formed was tested for L-lysine concen-tration, the L-lysine concentration was found to be 24 mg/dl. The results indicate that the ratio of solution of L-lysine into purified water was 36.9%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 61% and the ratio of solution to be 100% respectively.

Example 11

A solution of 294.4 g of calcium chloride.dihydrate in 300 ml of water was added to a liquid obtained by mixing 4386 g of an aqueous L-lysine base solution (20 wt % in concentration) with 203.9 g of sodium hexametaphosphate. The gel precipitate which consequently occurred was separated by filtration, washed with 12000 ml of water, and then dried at 60° C. under a reduced pressure to obtain 238 g of a white powder. When 1 g of the white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concentration, the concentration was found to be 125 mg/dl, indicating that the L-lysine content was 12.5%. When 1.00 g of this white powder was mixed with 100 ml of purified water, the resultant mixture was subjected to an ultrasonic treatment for five minutes, and the supernatant consequently formed was tested for L-lysine concentration, the L-lysine concentration was found to be 7 mg/dl. The results indicate that the ratio of solution of L-lysine into purified water was 5.6%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 92% and the ratio of solution to be 100% respectively.

Example 12

To a solution of 466.6 g of an aqueous L-lysine base solution (47 wt % in concentration) and 183.9 g of sodium tripoly-phosphate in 1000 ml of water, a solution having 9.26 g of calcium hydroxide and 147.2 g of calcium chloride.dihydrate dissolved and dispersed in 300 ml of water was added. The gel precipitate consequently formed was separated by filtration, washed with 12000 ml of water, and then dried at 60° C. under a reduced pressure to obtain 180 g of a white powder. When 1 g of the white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concentration, the concentration was found to be 98 mg/dl, indicating that the L-lysine content was 9.8%. When 1.00 g of this white powder was mixed with 100 ml of purified water, the resultant mixture was subjected to an ultrasonic treatment for five minutes, and the supernatant consequently formed was tested for L-lysine concentration, the L-lysine concentration was found to be 8 mg/dl. The results indicate that the ratio of solution of L-lysine into purified water was 8.1%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 89% and the ratio of solution to be 100% respectively.

Example 13

A solution having 259.3 g of calcium hydroxide dissolved in 500 ml of water was added to a liquid obtained by mixing 609 g of an aqueous L-lysine base solution (30 wt % in concentration) with 337.9 g of polyphosphoric acid ($H_6P_4O_{13}$) as cooled until neutralization. The resultant mixture evolved heat and gradually solidified wholly. The solid substance thus obtained was pulverized, washed with 12000 ml of water, and then dried at 60° C. under a reduced pressure to obtain 505.9 g of a white powder. When 1 g of the white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concentration, the concentration was found to be 165 mg/dl, indicating that the L-lysine content was 16.5%. When 1.00 g of this white powder was mixed with 100 ml of purified water, the resultant mixture was subjected to an ultrasonic treatment for five minutes, and the supernatant consequently formed was tested for L-lysine concentration, the L-lysine concentration was found to be 18 mg/dl. The results indicate that the ratio of solution of L-lysine into purified water was 11%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 85% and the ratio of solution to be 100% respectively.

Example 14

When 487 g of an aqueous L-lysine base solution (30 wt % in concentration) was mixed with 51.9 g of calcium hydroxide and 216 g of calcium dihydrogen pyrophosphate ($CaH_2P_2O_7$) and the resultant mixture was stirred and heated to 90° C., the produced mixture gradually solidified wholly. The solid substance consequently obtained was crushed, washed with 10000 ml of water, and then dried at 60° C. under a reduced pressure to obtain 356 g of a white powder. When 1 g of the white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concen-tration, the concentration was found to be 116 mg/dl, indicating that the L-lysine content was 11.6%. When 1.00 g of this white powder was mixed with 100 ml of purified water, the resultant mixture was subjected to an ultrasonic treatment for five minutes, and the supernatant consequently formed was tested for L-lysine concentration, the L-lysine concentration was found to be 27 mg/dl. The results indicate that the ratio of solution of L-lysine into purified water was 23%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 75% and the ratio of solution to be 100% respectively.

Example 15

A solution having 259.3 g of calcium hydroxide dispersed in 400 ml of water was added to a liquid obtained by mixing 292 g of an aqueous L-lysine base solution (50 wt % in concentration) with 337.9 g of polyphosphoric acid ($H_6P_4O_{13}$) and 150 g of water as cooled until neutralization. The produced mixture evolved heat and gradually solidified wholly. The solid substance thus obtained was crushed and dried at 60° C. under a reduced pressure to obtain 690 g of a white powder. When 1 g of the white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concen-tration, the concentration was found to be 212 mg/dl, indicating that the L-lysine content was 21.2%. When 1.00 g of this white powder was mixed with 100 ml of purified water, the resultant mixture was subjected to an ultrasonic treatment for five minutes, and the supernatant consequently formed was tested for L-lysine concentration, the L-lysine concentration was found to be 76 mg/dl. The results indicate that the ratio of solution of L-lysine into purified water was 36%. When this white powder was tested for protectiveness against the buffer solution equivalent to the gastric fluid in the first compart- ment of the stomach and for ratio of solution into the buffer solution equivalent to the gastric fluid in the fourth com- partment of the stomach, the ratio of protection was found to be 59% and the ratio of solution to be 100% respectively.

Example 16

A solution having 185.2 g of calcium hydroxide and 58.1 g of magnesium hydroxide dispersed in 350 ml of water was added to a liquid obtained by mixing 363 g of an aqueous L-lysine base solution (50 wt % in concentration) with 337.9 g of polyphosphoric acid ($H_6P_4O_{13}$) and 260 ml of purified water as cooled until neutralization. The produced mixture evolved heat and gradually solidified wholly. The solid substance thus obtained was crushed, washed with 12000 ml of water, and then dried at 60° C. under a reduced pressure to obtain 165 g of a white powder. When 1 g of the white powder was placed in 100 ml of purified water and the buffer solution equivalent to the gastric fluid in the first compart- ment of the stomach and stirred therein, it showed no sign of solution therein. When 1.00 g of this white powder was dissolved in 100 ml of dilute hydrochloric acid and the resultant solution was tested for L-lysine concen-tration, the concentration was found to be 126 mg/dl, indicating that the L-lysine content was 12.6%. When 1.00 g of this white powder was mixed with 100 ml of purified water, the resultant mixture was subjected to an ultrasonic treatment for five minutes, and the supernatant consequently formed was tested for L-lysine concentration, the L-lysine concen- tration was found to be 2.6 mg/dl. The results indicate that the ratio of solution of L-lysine into purified water was 2.1%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 97% and the ratio of solution to be 100% respectively.

Example 17

A solution having 166.7 g of calcium hydroxide dispersed in 300 ml of water was added to a liquid obtained by mixing 363 g of an aqueous L-lysine base solution (50 wt % in concentration) with 467 g of metaphosphoric acid [$(HPO_3)_n$] and 200 ml of purified water as cooled until neutralization. The produced mixture evolved heat and gradually solidified wholly. The solid substance thus obtained was crushed, washed with 12000 ml of water, and then dried at 60° C. under a reduced pressure to obtain 295 g of a white powder. When 1 g of the white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concentration, the concentration was found to be 99 mg/dl, indicating that the L-lysine content was 9.9%. When 1.00 g of this white powder was mixed with 100 ml of purified water, the resultant mixture was subjected to an ultrasonic treatment for five minutes, and the supernatant consequently formed was tested for L-lysine concentration, the L-lysine concentration was found to be 2.4 mg/dl. The results indicate that the ratio of solution of L-lysine into purified water was 2.4%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 96% and the ratio of solution to be 100% respectively.

Example 18

Figure 2:
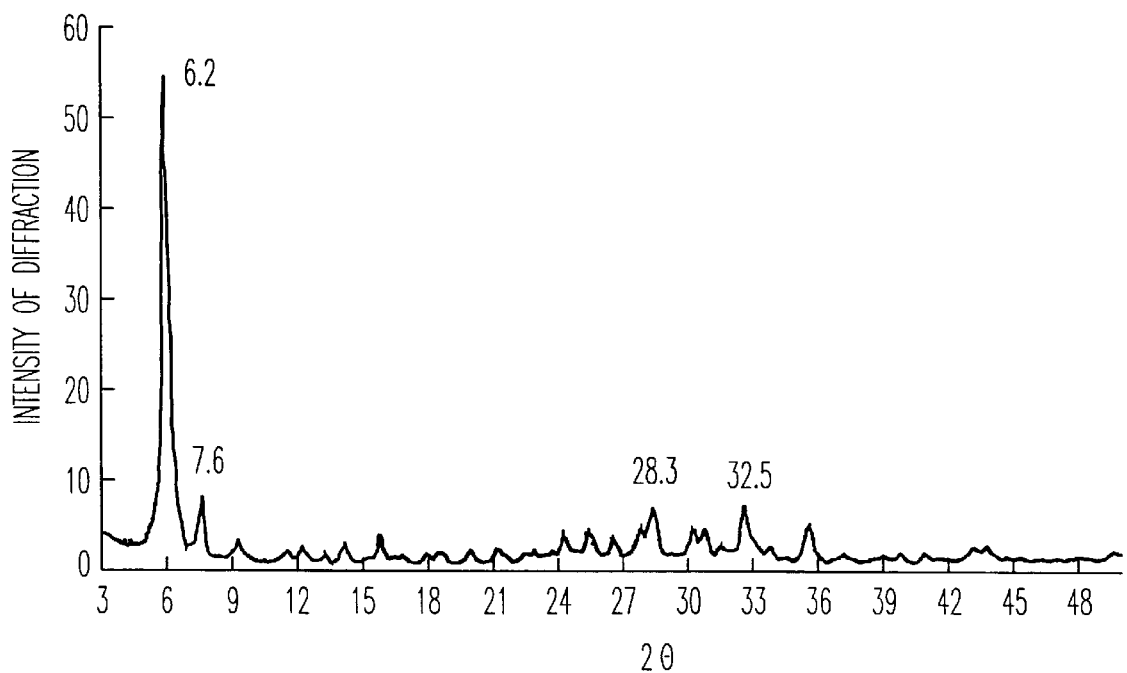
FIG. 2 is a powder X-ray diffraction chart of the novel phosphoric acid-amino acid complex compound of this invention obtained in Example 3.
Figure 3:
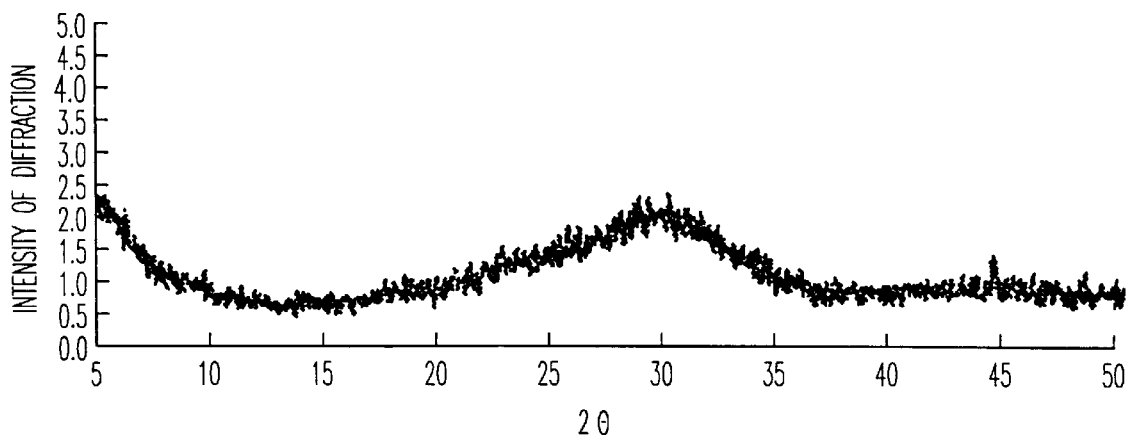
FIG. 3 is a powder X-ray diffraction chart of the novel phosphoric acid-amino acid complex compound of this invention obtained in Example 13.
Figure 4:
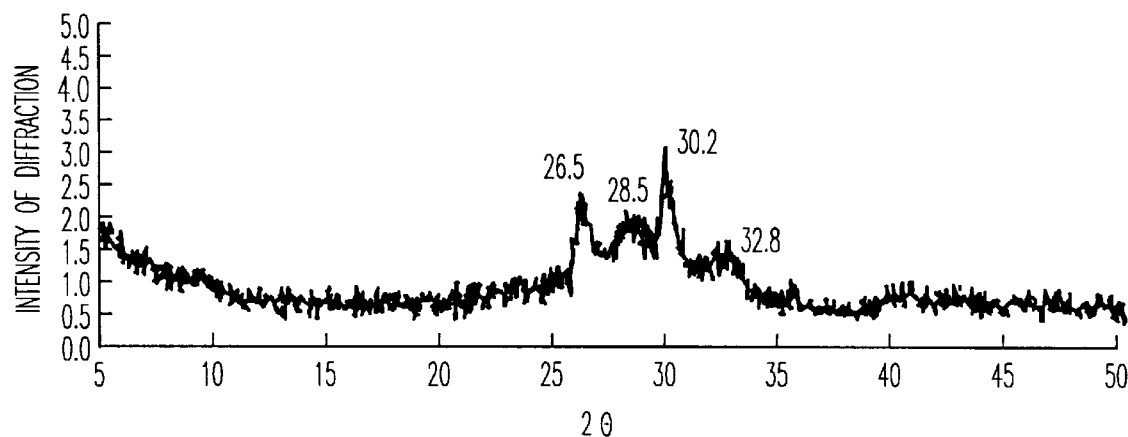
FIG. 4 is a powder X-ray diffraction chart of the novel phosphoric acid-amino acid complex compound of this invention obtained in Example 14.
Figure 5:
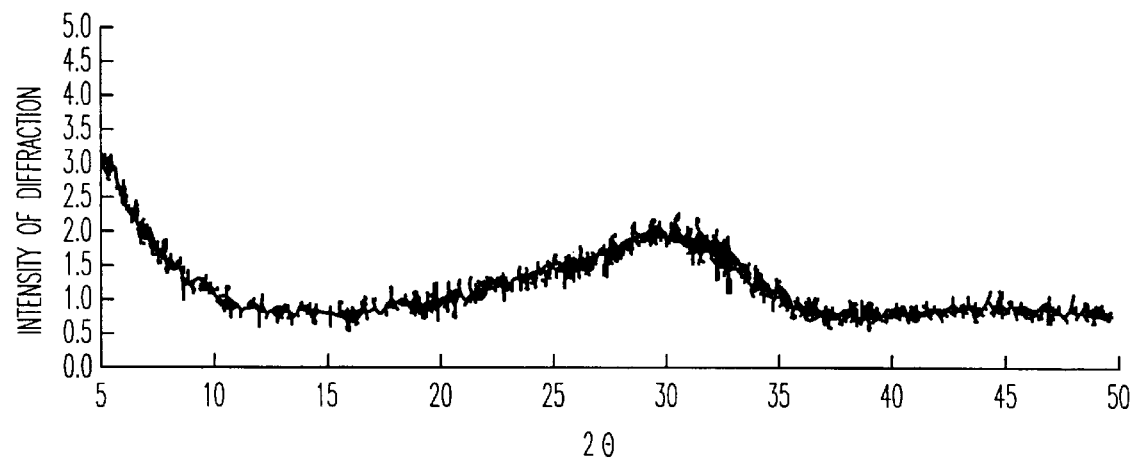
FIG. 5 is a powder X-ray diffraction chart of the novel phosphoric acid-amino acid complex compound of this invention obtained in Example 17.

The white powders obtained in Examples 11 through 17 were analyzed. The results of the analysis are shown in Table 2. The lysine content of a given sample was determined by dissolving the sample in dilute hydrochloric acid and ana- lyzing the resultant solution by liquid chromatography. The data on the ratio of solution into purified water, the protec- tiveness against the buffer solution equivalent to the gastric fluid in the first compartment of the stomach, and the solubility in the buffer solution equivalent to the gastric fluid in the fourth compartment of the stomach are shown addi- tionally in Table 1. The white powders obtained in Example 1, Example 3, Example 13, Example 14, and Example 17 were tested each for powder X-ray diffraction spectrum using a copper Kα ray. The spectral charts consequently obtained are shown respectively in FIGS. 1 through 5. The angles of diffraction (2Θ) and the relative ratios of intensity of the main peaks detected in the charts are shown collec- tively in Table 3. The detected main peaks invariably failed to coincide with the powder X-ray peaks obtained of the relevant raw materials and the homologous phosphates containing no basic amino acid.

TABLE 2

Analyses and physical properties of amino acid complex salt

Unit: wt%

| Example | 11 | 2 | 13 | 14 | 15 | 16 | 17 |
|---|---|---|---|---|---|---|---|
| Condensed phosphoric acid or metaphosphoric acid used | Sodium hexametaphosphate | Sodium tripolyphosphate | Polyphosphoric acid | Calcium hydrogen pyrophosphate | Polyphosphoric acid | Polyphosphoric acid | Metaphosphoric acid |
| Water content | 8.6 | 8.3 | 9.0 | 8.7 | 10.4 | 12.5 | 15.5 |
| Content other than water content | 91.4 | 91.7 | 91.0 | 91.3 | 89.6 | 87.5 | 84.5 |
| Lysine content | 12.5 | 9.8 | 16.5 | 11.6 | 21.2 | 12.6 | 9.9 |
| Calcium content (magnesium) | 24.1 | 24.4 | 19.4 | 26.8 | 20.9 | 17.6 (4.0) | 23.2 |
| Phosphorus content | 20.3 | 20.5 | 19.6 | 19.8 | 18.4 | 19.9 | 23.8 |
| Separability into pure water | 5.6% | 8.1% | 10.9% | 23.3% | 35.8% | 2.1% | 2.4% |
| Protectiveness in first compartment of the stomach | 92% | 89% | 85% | 75% | 59% | 97% | 96% |
| Separability in fourth compartment of the stomach | 100% | 100% | 100% | 100% | 100% | 100% | 100% |

TABLE 3

| Example | 1 | 3 | 13 | 14 | 16 |
|---|---|---|---|---|---|
| Angle of diffraction (2Θ) of main peak and relative strength ratio to maximum peak | 3.8° (41.8) 7.4° (100) 11.5° (3.7) 18.5° (8.4) 18.8° (9.8) 19.7° (7.0) 20.7° (9.6) 21.2° (6.4) 22.2° (8.0) 29.7° (11.8) 32.3° (8.1) 37.4° 37.9° (4.9) | 6.2°* (100) 7.60 (11.8) 9.2° (4.2) 15.6° (5.0) 24.2° (4.1) 25.4° (4.7) 26.5° (3.8) 28.3° (10.4) 32.5° (10.3) | A slight bulge of large width in the range of 20° to 35+ | 26.5** (66) 28.5°** (56) 30.2°** (100) 32.8°** (36) | A slight bulge of large width in the range of 20° to 35+ |

The peak of the mark * in the table indicates a change in the angle of diffraction in the range of 5.9° to 6.7°, depending on the drying condition of a relevant powder.
The peak of the mark ** in the table shows a larger error than the other peaks due to a low intensity of diffraction.

Example 19

When a solution having 72.9 g of magnesium hydroxide dispersed thorough in 200 ml of water was mixed with a solution of 174.2 g of L-arginine and 98.0 g of phosphoric acid (85% in concentration in 300 ml of water, an exothermic reaction ensued to produce a white solid substance. This white solid substance was heated at 95° C. for three hours and then disintegrated thoroughly in 1000 ml of purified water. The solid phase formed consequently was separated by filtration, washed with 1000 ml of water, and then dried at 60° C. under a reduced pressure to obtain 235 g of a white powder. When 1 g of this white powder was placed in 100 ml of purified water and the buffer solution equivalent to the gastric fluid in the first compartment of the stomach and stirred therein, it showed no sign of solution therein. When 1.00 g of this white powder was dissolved in 100 ml of dilute hydrochloric acid and the resultant solution was tested for L-lysine concentration, the concentration was found to be 370 mg/dl, indicating that the L-lysine content was 37.0%. When 1.00 g of this white powder was mixed with 100 ml of purified water, the resultant mixture was subjected to an ultrasonic treatment for five minutes, and the supernatant consequently formed was tested for L-lysine concentration, the L-lysine concentration was found to be 100 mg/dl. The results indicate that the ratio of solution of L-lysine into purified water was 27.0%. When this white powder was tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 30% and the ratio of solution to be 100% respectively.

Example 20

Grains of a diameter of about 1 mm were produced by mixing 200 g of the white crystalline powder obtained in Example 1 with 150 g of hardened soybean oil, extruding the resultant mixture through a die 1 mm in diameter at 65° C. by the use of a hot extruding device, and chopping the extruded thread of mixture into lengths of about 1 mm. When the granules thus obtained were tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 35% and the ratio of solution to be 95% respectively.

Example 21

Granules of a diameter of about 2 mm were produced by mixing 300 g of the white powder obtained in Example 3 with 20 g of methionine powder, 50 g of calcium carbonate, 30 g of casein sodium and 5 g of starch sodium glycolate, kneading the resultant mixture with 100 ml of water, extruding the produced dough by means of a disc pelleter 2 mm in diameter, chopping the extruded thread of dough into lengths of about 2 mm, and drying the chopped pieces. The granules thus obtained were divided by a cutter into small pieces about 0.5 mm in diameter. Five of these small pieces were each heated and extracted with dilute hydrochloric acid and tested for amino acid content. No difference in amino acid content was found among these five small pieces. When the granules obtained as described above were tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 97% with respect to lysine and 64% with respect to methionine and the ratio of solution to be 95% with respect to both lysine and methionine. When the small pieces about 0.5 mm in diameter were similarly tested for protectiveness against the buffer solution equivalent to the gastric fluid in the first compartment of the stomach and for ratio of solution into the buffer solution equivalent to the gastric fluid in the fourth compartment of the stomach, the ratio of protection was found to be 95% with respect to lysine and 62% with respect to methionine and the ratio of solution to be 98% with respect to both lysine and methionine.

EFFECT OF THE INVENTION

By preparing a complex salt which is composed of a basic amino acid, an alkaline earth metal, and phosphoric acid and consequently enabled to manifest insolubility in a neutral to alkaline aqueous solution and solubility in an acidic aqueous solution as described above, an additive composition for use in a feed for ruminant mammals is obtained which contains such basic amino acids as lysine, i.e. substances frequently missing in the conventional feed for ruminant mammals, and which excels in protection in the first compartment of the stomach and in solubility in the fourth compartment of the stomach. The homogeneous grains according to this invention are not easily broken even when they are exposed to the impacts of ruminant mastication or mixture with other feed components. The present invention is capable of producing an additive composition for use in a feed for ruminant mammals which is excellent in protection in the first compartment of the stomach and solubility in the fourth compartment of the stomach as compared with the additive composition produced by the conventional technique. Thus, this invention provides a feed additive which enables a biologically active substance to be effectively absorbed by ruminant mammals and makes a very significant contribution to economy.

We claim:
1. A salt having formula (1):

$$R_aM_bH_cPO_4nH_2O \qquad (1)$$

wherein R represents cationic lysine; M represents ionic magnesium; a is a number in the range of 0.05 to 1; b is a number in the range of 1 to 1.47; c is a number in the range of 0 to 0.3; a, b and c collectively satisfy the equation $$a+(2\times b)+c=3;$$

and n is a number in the range of 0 to 10.

2. The salt of claim 1, wherein a is 1, b is 1, and c is 0.

3. The salt of claim 1, wherein a is a number in the range of 0.21 to 0.25, b is a number in the range of 1.325 to 1.395, and c is a number in the range of 0 to 0.1.

4. A composition for feed for a ruminant mammal, comprising the salt of claim 1 in an amount effective for feedings lysine.

5. The composition of claim 4, wherein a is 1, b is 1, and c is 0.

6. The composition of claim 4, wherein a is a number in the range of 0.21 to 0.25, b is a number in the range of 1.325 to 1.395, and c is a number in the range of 0 to 0.1.

7. The composition of claim 4, which is in the form of granules.

8. The composition of claim 7, wherein said salt maintains its high solubility in acidic water or aqueous solution.

9. The composition of claim 4, which further comprises a component selected from the group consisting of binders for forming granules, diluents, amino acids, veterinary medicines, vitamins, minerals, and fatty acids.

10. The composition of claim 4, which further comprises one or more biologically active substances.

* * * * *